United States Patent [19]

Christensen et al.

[11] 4,172,895
[45] Oct. 30, 1979

[54] 6-(1'-HYDROXYETHYL)-2-AMINOETH-YLTHIO-OXAPEN-2-EM-3-CARBOXYLIC ACID

[75] Inventors: Burton G. Christensen, Metuchen; Frank P. DiNinno, Old Bridge, both of N.J.

[73] Assignee: Merck & Co., Inc., Rahway, N.J.

[21] Appl. No.: 865,166

[22] Filed: Dec. 28, 1977

[51] Int. Cl.$^2$ .................. A61K 31/42; C07D 498/04
[52] U.S. Cl. .......................... 424/272; 260/239 A; 260/245.3; 260/245.2
[58] Field of Search .............. 424/272; 260/307 F

[56] References Cited

U.S. PATENT DOCUMENTS 3,950,357  4/1976  Kahan et al. .................. 260/326.27

OTHER PUBLICATIONS

Eglington—J.C.S. Chem. Comm. (1977), p. 720.

Primary Examiner—Raymond V. Rush
Attorney, Agent, or Firm—Hesna J. Pfeiffer; James A. Arno; Julian S. Levitt

[57] ABSTRACT

Disclosed is 6-(1'-Hydroxyethyl)-2-aminoethylthiooxapen-2-em-3-carboxylic acid:

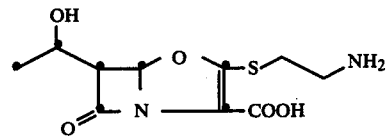

Such compound and its pharmaceutically acceptable salt and ester derivatives are useful as antibiotics. Also disclosed are processes for the preparation of such compounds pharmaceutical compositions comprising such compounds and methods of treatment comprising administering such compounds and compositions when an antibiotic effect is indicated.

2 Claims, No Drawings

6-(1'-HYDROXYETHYL)-2-AMINOETHYLTHIO-OXAPEN-2-EM-3-CARBOXYLIC ACID

BACKGROUND OF THE INVENTION

This invention relates to 6-(1'-hydroxyethyl)-2-aminoethylthio-oxapen-2-em-3-carboxylic acid and its pharmaceutically acceptable salts and esters, which compounds are useful as antibiotics and which may be represented by the following generic structural formula (I):

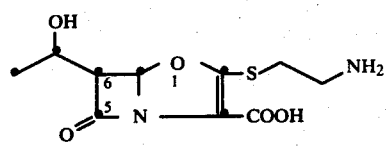

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

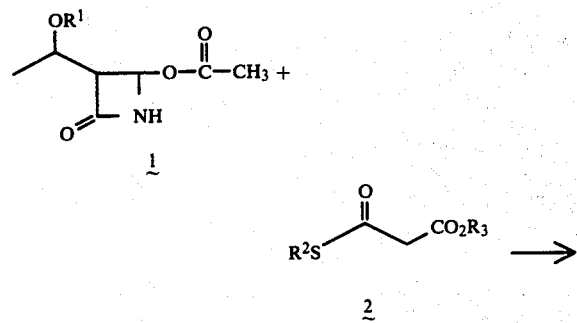

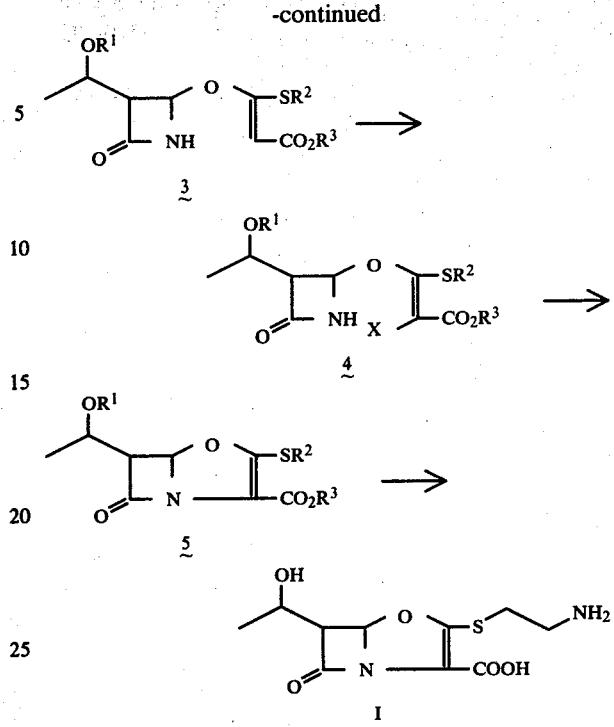

In words relative to the above diagram, the starting azetidinone 1 is treated with the malonic acid diester (2) in the presence of a base such as NaH, Al-[OCH(CH$_3$)$_2$]$_3$, lithium diisopropylamide and the like in a solvent such as dimethoxyethane, tetrahydrofuran (THF), dimethylformamide and the like at a temperature of from 0° to 22° C. for from 1 to 96 hours to provide the seco-lactam (3). Relative to these reactions, R$^1$ is a readily removable protecting group such as p-nitrobenzyloxycarbonyl, trichloroethoxycarbonyl, t-butyldimethylsilyl or the like; R$^3$ is a readily removable carboxyl blocking group such as p-nitrobenzyl, t-butyl, trichloroethyl or the like; and R$^2$ is —CH$_2$CH$_2$NHR$^4$ wherein R$^4$ is a readily removable acyl protecting group such as p-nitrobenzyloxycarbonyl, t-buyoxycarbonyl, trichloroethoxycarbonyl or the like. Halogenation of 3 yields 4 wherein X is halo, such as chloro or bromo. Suitable halogenating agents include N-chlorosuccinimide, N-bromosuccinimide, N-bromoacetamide and the like; and the reaction 3→4 is conducted in the presence of the halogenating agent of choice in a solvent such as THF, benzene, benzene-ether and the like at a temperature of from 0° to 60° C. for from 0.5 to 24 hours. Cyclization of 4 to provide 5 is accomplished by treating 4 with a strong base such as lithiumdiisopropylamide, lithiumhexamethyldisilazide, lithiumtetramethylpiperidide or the like in a solvent such as tetrahydrofuran, hexamethylphosphoramide, dimethoxyethane or the like in the presence of cuprous iodide, cuprous bromide-dimethylsulfide complex, cuprous iodide-tri-n-butylphosphine complex or the like at a temperature of from −78° to 22° C. for from 0.5 to 18 hours. The fully protected intermediate 5 is deblocked to provide I. When the preferred blocking groups are employed, that is, R$^1$ is p-nitrobenzyloxycarbonyl or trichloroethoxycarbonyl; R$^4$ is p-nitrobenzyloxycarbonyl or trichloroethoxycarbonyl and R$^3$ is p-nitrobenzyl or trichloroethyl, the deblocking reaction may be accomplished by hydrogenation or zinc mediated reduction according to well-known procedures. a representative deblocking procedure comprises treating 5 in a solvent such as ethylacetate under hydrogen (1–40 atmospheres) at a temperature of 0° to 22° C. for from 0.25 to 2 hours in the presence of a hydrogenation catalyst such at 10%Pd/C, 5%Pd/BaCo₃, 5%Pt/C or the like.

The starting azetidinone material 1 may conveniently be prepared by the following scheme:

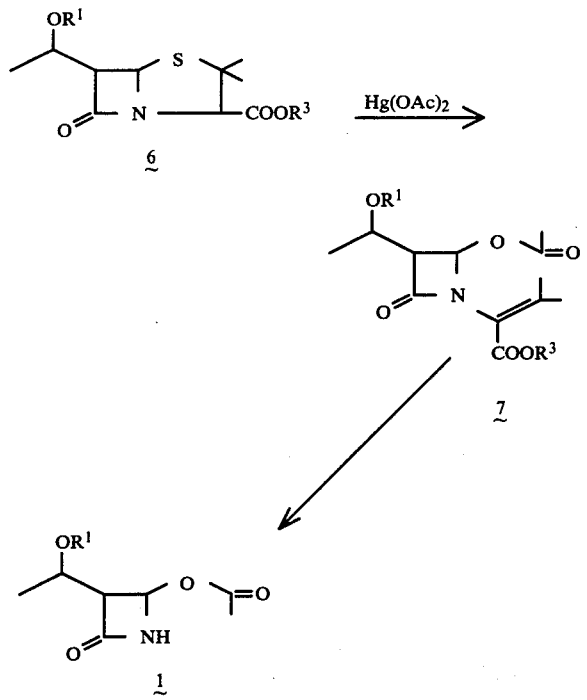

wherein R¹ and R³ are as defined above; the preparation of starting material 6 is given below in the Examples section.

In words relative to the above diagram, starting material 6 is cleaved with mercuric acetate in acetic acid solution at a temperature of from 22° C. to 110° C. for from 0.25 hours to 8 hours to provide the acetoxy lactam 7. Relative to these reactions, R¹ is a readily removable protecting group such as p-nitrobenzyloxycarbonyl, trichloroethoxycarbonyl, t-butyldimethylsilyl or the like; R³ is a selected carboxyl protecting group such as methyl, benzyl, trichloroethyl or the like. Removal of the isopropylidene ester function is accomplished by treating 7 with potassium permanganate, osmium tetraoxide or the like in a solvent such as aqueous pyridine, aqueous acetone or the like at a temperature of 0° to 22° C. for from 0.25 to 2 hours, to provide azetidinone 1. Analogous procedures are known in the literature; see, for example: E. G. Brain, et al., *J. Chem. Soc., Perkin I*, 447 (1976); R. J. Stoodley and N. R. Whitehouse, Ibid., 32 (1973).

Starting material 2 in the above-described synthesis may conveniently be prepared by the following scheme:

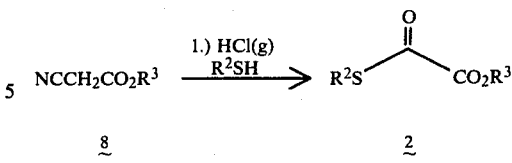

wherein R² is —CH₂CH₂NHR⁴ and R², R³ and R⁴ are as defined above.

In words relative to the above diagram, the cyanoacetic acid ester 8 is treated with gaseous hydrogen chloride in a solvent such as benzene, diethylether, tetrahydrofuran or the like in the presence of a nitrogen protected cysteamine derivative, HSCH₂CH₂ₕNR₄, (R²SH) at a temperature of from 0° C. to 25° C. for from 0.25 to 1 hour. The resulting mixture is stirred at a temperature of from 0° to 80° C. for from 8 to 96 hours. The precipitate is collected by filtration, redissolved in dimethylsulfoxide, dimethylformamide or the like, and treated with aqueous hydrochloric acid, aqueous trifluoroacetic acid or the like at a temperature of from 25° to 80° C. for from 0.25 to 24 hours to afford 2.

The preferred ester moieties, R³, (see 5 above) used as carboxyl protecting groups are those wherein R³ is benzyl, p-nitrobenzyl, o-nitrobenzyl, t-butyl, bromo-t-butyl, t-butyl-dimethylsilyl, trimethylsilyl, trichloroethyl; R³ may also represent pharmaceutically acceptable ester moieties such as pivaloyloxymethyl, allyl, methallyl, (2-methylthio)-ethyl, or 3-buten-1-yl.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried by I are also contemplated. Such pharmaceutically acceptable acid addition salts are derived from organic and inorganic acids such as Cl, HBr, citric, tartaric and the like.

The salts can be mono-salts such as the mono- sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 6-(1'-hydroxyethyl)-2-aminoethylthiooxapen-2-em-3-carboxylic acids of the present invention are valuable antimicrobial substances which are active against various gram-positive and gram-negative pathogens. Thus, the free acid and especially the salts thereof such as amino and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus*. The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternately, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All temperatures are in °C.

EXAMPLE 1

Preparation of Azetidinone 1

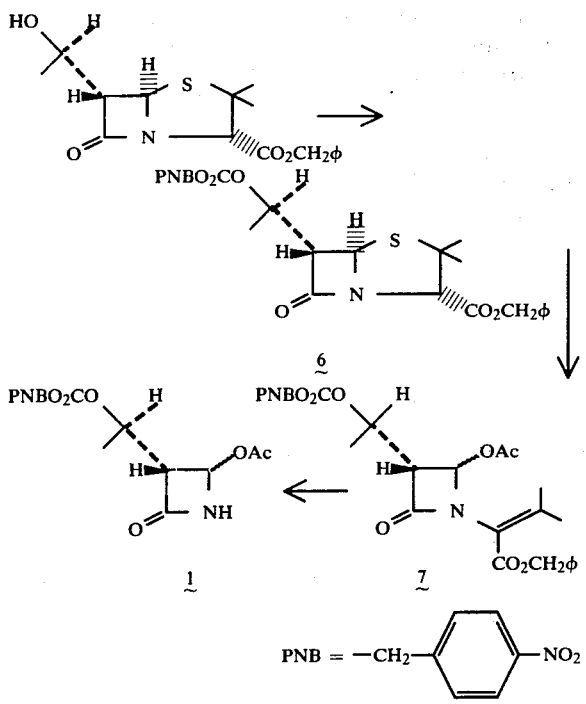

Step A, Preparation of 6

To a stirred solution of 215 mg. (0.6 mmol) of benzyl-6α-[(R)-1′-hydroxyethyl]penicillanate [DiNinno, et al., J. Org. Chem. 42, 2960 (1977)] and 276 mg (0.13 mmol) p-nitrobenzylchloroformate in 5 ml dry methylene chloride at 0° C. is added in one portion solid 4-dimethylaminopyridine (156 mg., 0.13 mmole). The mixture is stirred at 0° C. under a nitrogen atmosphere for 2 min. and allowed to warm over 28 min. The mixture is poured into ice-H$_2$O and extracted with CH$_2$CH$_2$. The organic phase is separated and washed successively with cold, dilute, aqueous HCl and saturated NaCl (aq.). After drying with MgSO$_4$, the filtered solution is evaporated and dried in vacuo to give 420 mg of residue. Purification by plate layer chromatography [development C$_6$H$_6$-EtOAc(9:1)] provides 278.2 mg. (84% of product 6; ir (CHCl$_3$) 1770, 1740 cm; nmr (CDCl$_3$) 1.4, 3H(s); 1.48, 3H(d, J=6Hz); 1.61, 3H(s); 3.46, 1H(dd, J=2, 7Hz); 4.5, 1H(s); 5.2, 2H(s); 5.23, 1H(m); 5.27, 2H(s); 5.31, 1H(d, J=2Hz); 7.37, 5H(s); 7.53, 2H(d, J=8Hz); 8.23, 2H(d, J=8Hz).

Step B

Preparation of 7

A stirred mixture of 186.8 mg (0.36 mmol) of 6 and 232 mg. (0.73 mmol) Hg(OAc)$_2$ (mercuric acetate) in 7 ml glacial HOAc (acetic acid) is heated at 90° C. for 1.5 hour under a nitrogen atmosphere. The cooled mixture is filtered through supercel, washing thoroughly with CH$_2$Cl$_2$. The filtrate is diluted with H$_2$O and is neutralized with solid NaHCO$_3$. The mixture is extracted thoroughly with CH$_2$Cl$_2$ and the combined extracts are washed successively with saturated NaHCO$_3$ (aq.) and saturated NaCl (aq.). After drying with MgSO$_4$, the filtered solution is evaporated and the residue so obtained is purified by plate layer chromatography [development CHCl$_3$-EtOAc(20:1)] to provide 138.6 mg (71%) of approximately a 1:1 mixture of cis and trans-acetoxyazetidinones 7; ir (CHCl$_3$) 1770, 1750, 1730; nmr (CDCl$_3$) 1.4 and 1.53, 3H(d's, J's=6Hz and 7Hz); 1.86, 1.96 & 2.0 (6H(s); 2.23 3H(s); 3.4 & 3.58, 1H(dd's, J's=2,7Hz & 4,10Hz); 5.2, 1H(m); 5.2, 2H(s); 5.23, 2H(s); 6.23 & 6.3, 1H(d's, J's=2 & 4Hz); 7.3, 5H(s); 7.53, 2H(d, J=8Hz); 8.2, 2H(J=8Hz); mass spectrum m/e 540(M$^+$), 498, 390, 346, 301, 222, 210, 193, 136, 91.

Step C

Preparation of 1

To a stirred solution of 138.6 mg (0.26 mmol) of azetidinones 7 in 3.5 ml of 8:1(CH$_3$)$_2$CO—H$_2$O and 1 drop of pH 7 0.1 N phosphate buffer at room temperature (25° C.) is added 40.6 mg (0.26 mmol) of solid KMnO$_4$. The mixture is stirred under a nitrogen atmosphere at 25° C. for 8 min. After this time, 40.6 mg (0.26 mmol) of additional KMnO$_4$ is added and the mixture is stirred further for 45 min. The reaction mixture is diluted with EtOAc (ethylacetate) and treated with cold, aqueous Na$_2$S$_2$O$_3$ until the violet coloration of KMnO$_4$ is no longer apparent. The mixture is filtered through celite and is washed well with EtOAc. The filtrate is washed with saturated NaCl (aq.), dried (MgSO$_4$), filtered, and evaporated. Purification of the residue by plate layer chromatography [development CHCl$_3$—EtOAc(3:1)] gives 65.5 mg. (72%) of the azetidinone mixture 1: ir (CHCl$_3$) 3300, 1785, 1750 cm$^{-1}$; nmr (CDCl$_3$), 1.5 & 1.53, 3H(d's, J's-7Hz); 1.98 & 2.12, 3H(S); 2.43, (dd, J=2, 6Hz) & 2.65, (dq, J=1.5, 4.0, 9Hz) [1H]; 5.28, 2H(S); 5.3, 1H(m); 5.88 & 5.95, 1H(d's, J's=1.5 & 4.0Hz); 6.93, 1H(bs); 7.57, 2H(d, J=8Hz); 8.25, 2H(d, J=8Hz); mass spectrum m/e 309, 292, 249, 181, 154, 136.

EXAMPLE 2

Preparation of 6-α-[(R)-1′hydroxyethyl]-2-aminoethylthio-oxapen-2-em-3′-carboxylic acid (I)

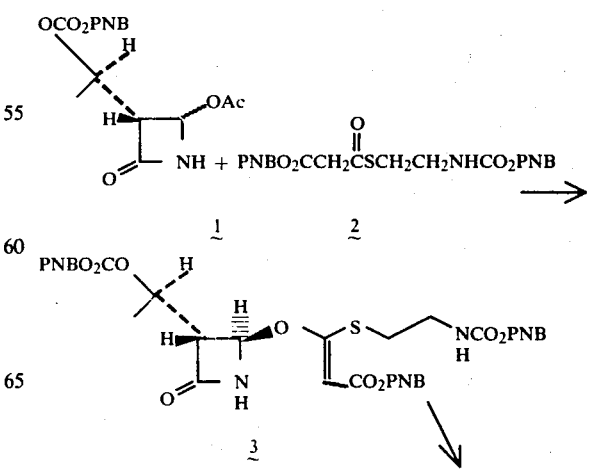

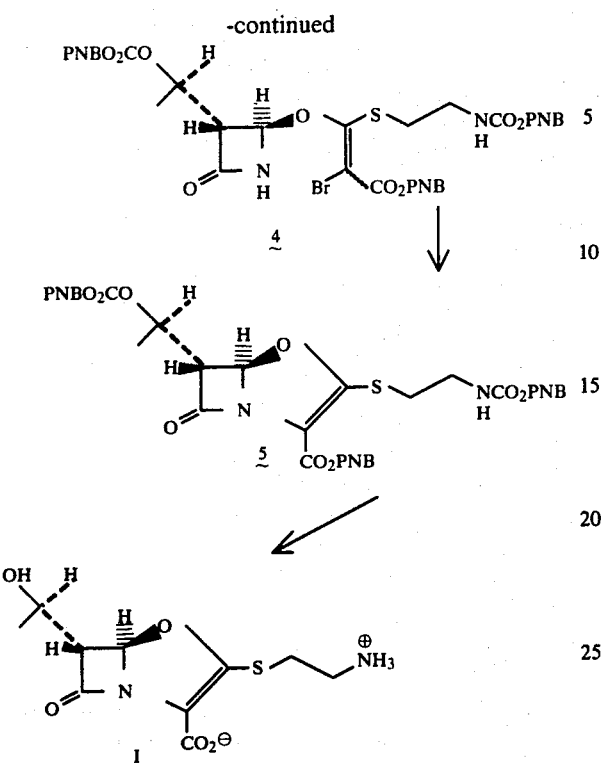

Step A

Preparation of 2

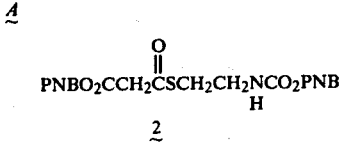

To a stirred solution of 3.77 g (77.2 mmol) of p-nitrobenzylcyanoacetate and 4.0 g (15.6 mmol) of N-p-nitrocbzcysteamine (A) in 40 ml dry benzene at 25° C. under a nitrogen atmosphere is introduced a stream of HCl (g) for 7 min. The reaction mixture is cooled on an ice water bath and the introduction of HCl (g) continued for 3 min. The ice water bath is removed and the mixture is stirred magnetically for 24 hrs. After this time, the solution is removed from the separated solid with the aid of a filter stick and the solid is washed with dry benzene (2×40 ml) in the same manner. The solid is dried in vacuo in the reaction flask, then dissolved in dimethylsulfoxide (DMSO) at 25° C. and treated with 2.5 N aq. HCl for 3 hr. The mixture is poured into diethyl ether and ice-water. The organic phase is separated and washed with water (4X) and saturated sodium chloride (aq.) solution. The organic phase is dried (MgSO$_4$), filtered and evaporated. Purification by column chromatography to yield 2: NMR (CDCl$_3$)δ: 3.0–3.6 (4H,m), 3.7 (2H,s), 5.17 (2H, s), 5.27 (2H,s), 7.47 (4H, d, J=8Hz), 8.17 (4H, d, J=8Hz); m/e 341 (M+ −136), 256, 239, 209, 195, 165, 153, 136.

Step B

Preparation of Seco-Lactam 3

To a stirred mixture of 62.2 mg (0.18 mmol) of azetidinones 1 and 85.9 mg (0.18 mmol) of 2 in 1.5 ml of dry THF at 25° C. is added in one portion 50.5 mg (0.25 mmol) of solid aluminum isoproproxide [Al(O-≺)$_3$]. The mixture is stirred at 25° C. under N$_2$ for 66.0 hr. and is then partitioned between EtOAc and a cold, aqueous solution of dilute HCl-tartaric acid mixture. The EtOAc phase is separated and is washed with saturated NaCl-(aq.), dried (MgSO$_4$), filtered, and evaporated. Purification by plate layer chromatograhy provides 3.

Step C

Preparation of Bromide 4

To a stirred solution of lactam 3 0.085 mmol) and 15.1 mg (0.085 mmol) HMPA (hexmethylphosphoramide in 2.0 ml dry THF (tetrahydrofuran) at 25° C. is added in one portion 16.5 mg (0.093 mmol) solid NBS (N-bromosuccinimide). The mixture is stirred at 25° C. under N$_2$ for 16 hr. and evaporated. The residue is partitioned between EtOAc and H$_2$O and the EtOAc phase is separated. It is further washed with H$_2$O (2x) and saturated NaCl (aq.), then dried (MgSO$_4$), filtered, and evaporated. Purification by repetitive plate layer chromatography affords 4.

Step D

Preparation of Oxapenem 5

To a stirred mixture of 33.9 mg (0.04 mmol) of bromide 4 and 28 mg (0.14 mmol) of CuBr.S(CH$_3$)$_2$ in 5 ml dry THF at −78° C. under N$_2$ is added 2 ml of a cold, freshly prepared solution of lithium diisopropylamide, LiN(-≺ )$_2$, [generated at 0°/20 min. with 5 mg (0.05 mmol) HN(-≺ )$_2$ (diisopropylamide) and 19 μl of 2.4 M buLi (butyllithium)]. The mixture is stirred over the following temperature ranges for the times indicated: −78° to −74° (40 min.); −74° to −68° (30 min.); −68° to −57° (30 min.); −57° to −41° (20 min.); −41° to −26° (20 min.); −26° to −20° (28 min.); −20° to −13°, (38 min.); −15° to −9° (53 min.); −10° to −5° (18 min.); and −5° to 0° (18 min.). The mixture is then treated at 0° with 1ml of saturated NH$_4$Cl (aq.) and diluted with Et$_2$O/H$_2$O. The organic phase is separated and washed further with aqueous NH$_4$Cl and saturated NaCl (aq.). The organic layer is dried (MgSO$_4$), filtered, and evaporated. The residue is purified by plate layer chromatography to afford oxapenem 5.

Step E

Preparation of Oxapenem I

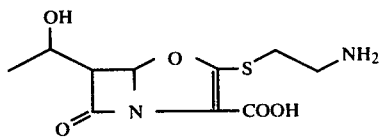

To 20 mg 5 (Step D, above) is added 0.60 ml dioxane, 0.05 ml ethanol, 0.35 ml deionized water and 0.01 ml of 1.0 M K$_2$HPO$_4$. To the resultant clear solution is added 5 mg of 10% Pd/C. The suspension is flushed with N$_2$, then 5–6 times alternately with 50 psi H$_2$ and vacuum. Finally, it is shaken under a 50 psi H$_2$ atmosphere for 30–40 min. After centrifugation, the Pd/C is washed and centrifuged 2–3× with 0.5 ml portions of deionized water. The combined centrifugates are extracted 5×1–2 ml ether. Residual ether is removed under vacuum and the aqueous solution applied to an XAD-2 column (20×140 mm). Fractions of 100 drops (6–7 ml) are collected, with continuous UV monitoring, by elution with deionized water. The chosen fractions are combined and lyophilized to provide I.

EXAMPLE 3

Preparation of Pharmaceutical Compositions

One such unit dosage form consists in mixing 120 mg. of 6-(1'-hydroxyethyl)-2-aminoethylthio.oxapen-2-em-3-carboxylic acid with 20 mg. of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-(1'-hydroxyethyl)-2-aminoethylthio-oxapen-2-em-3-carboxylic acid | 125 mg. |
| Dicalcium Phosphate | 192 mg. |
| Cornstarch, U.S.P. | 6 mg. |
| Lactose, U.S.P. | 190 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION

Ampoule:
6-(1'-hydroxvethyl)-2-aminoethylthio-oxapen-2-em-3-carboxylic acid—500 mg.
Diluent: Sterile Water for Injection—2 cc

OPTHALMIC SOLUTION 6-(1'-hydroxyethyl)-2-aminoethylthiooxapen-2-em-3-carboyxlic acid—100 mg.
Hydroxypropylmethyl cellulose—5 mg.
Sterile Water—to 1 ml.

OTIC SOLUTION 6-(1'-hydroxyethyl)-2-aminoethylthiooxapen-2-em-3-carboxylic acid—100 mg.
Benzalkonium chloride—0.1 mg.
Sterile Water—to 1 ml.

TOPICAL OINTMENT 6-(1'-hydroxyethyl)-2-aminoethylthiooxapen-2-em-3-carboxylic acid—100 mg.
Polyethylene Glycol 4000 U.S.P.—400 mg.
Polyethylene Glycol 400 U.S.P.—1.0 gram The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

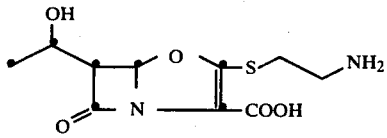

and the pharmaceutically acceptable salts thereof.

2. A pharmaceutical composition comprising a compound according to claim 1 and a pharmaceutical carrier therefor.

* * * * *